United States Patent [19]

Taylor et al.

[11] Patent Number: 5,428,172
[45] Date of Patent: Jun. 27, 1995

[54] PREPARATION OF 3-DIHALOACETYL OXAZOLIDINES

[75] Inventors: William D. Taylor, Kirkwood; Bruce J. Gaede, University City, both of Mo.

[73] Assignee: Monsanto Company, St. Louis, Mo.

[21] Appl. No.: 124,067

[22] Filed: Sep. 21, 1993

[51] Int. Cl.$^6$ ............................................ C07D 263/06
[52] U.S. Cl. ..................................... 546/275; 548/215
[58] Field of Search ................ 548/215, 216; 564/495; 546/275

[56] References Cited

U.S. PATENT DOCUMENTS

| | | | |
|---|---|---|---|
| 2,157,386 | 5/1939 | Johnson | 564/495 |
| 2,347,621 | 4/1944 | Tindall | 548/215 |
| 2,587,572 | 2/1952 | Tyron | 564/495 |
| 3,402,203 | 9/1968 | Tindall | 548/215 |
| 3,564,057 | 2/1971 | Tindall | 548/215 |
| 4,038,284 | 7/1977 | Pitt | 548/215 |
| 4,069,036 | 1/1978 | Dorschner et al. | 548/215 |

OTHER PUBLICATIONS

Bergmann, Chemical Reviews vol. 53, pp. 309, 318–319, 328–331 (1953).

*Primary Examiner*—Donald G. Daus
*Attorney, Agent, or Firm*—William I. Andress; Richard H. Shear

[57] ABSTRACT

The disclosure herein relates to a new process for the preparation of 3-dihaloacetyl (un)substituted oxazolidine compounds by the catalytic hydrogenation of nitroalcohols with aldehydes or ketones followed by reaction with a dihaloacetyl halide.

10 Claims, No Drawings

PREPARATION OF 3-DIHALOACETYL OXAZOLIDINES

FIELD OF THE INVENTION

The invention herein relates to the field of 3-dihaloacetyl oxazolidines and to a process for the preparation thereof.

BACKGROUND OF THE INVENTION

3-Dihaloacetyl oxazolidine compounds prepared herein are known compounds; they are particularly useful as antidotal (safener) compounds to lessen or eliminate injury to crop plants by herbicidal compounds.

The 3-dihaloacetyl oxazolidine compounds discussed herein have been prepared by a variety of processes, all of which proceed through the corresponding non-haloacetylated precursor oxazolidine compound. The latter compounds have been prepared by the reaction of mono- and dihydric amino alcohols, e.g., ethanolamine or propanolamine, and an aldehyde, such as acetaldehyde, or a ketone, such as acetone. Such processes have been disclosed, e.g., by M. Senkus, J.A.C.S. 67 1515–1519 (1945) E. D. Bergmann, Chem. Rev. 53,309–352, especially 310–315, (1953) and by I. E. Saavedra, J. Org. Chem,. 1985, 50, 2379.

In adaptations of the above Senkus and Bergmann processes, K. D. Petrov et al. (Chem. Abs. 68 3840 (1967) describe the preparation of 3-(2-hydroxyethyl) oxazolidine by the reaction of furfurylaminoethanol or tetrahydrofurfurylaminoethanol and dihydroxyethylamine. Also described by Petrov et al are modifications involving the reaction of N-(2-hydroxyethyl) oxazolidine with the appropriate aldehyde, ketone or $RCO_2Et$ ester containing sodium to prepare oxazolidine compounds substituted in the 3-position (i.e., the N atom), e.g., with such radicals as $C_3H_7CO_2C_2H_5$-, $C_6H_6OCH_2$-, etc.

The above process is also described in various patents which further show the reaction of the formed oxazolidine with a dihaloacetyl halide compound, typically dichloroacetyl chloride, to produce the corresponding 3-dichloroacetyl-(un)substituted oxazolidine compounds. Representative of such prior art patents include U.S. Pat. Nos. 4,038,284 and 4,278,799; EP Patent Applications 0 136 016, 0021759 and 190105 and GB Patent No. 1,544,679.

Another process for producing 3-dichloroacetyl (un)-substituted oxazolidines includes the reaction of epichlorohydrin with the appropriate secondary amine (EP 0253 291).

Yet another process for preparing 3-dichloroacetyl oxazolidine which are characterized by having (un) substituted heterocyclic radicals in the 5-position is described in U.S. Pat. No. 5,225,570. The process described in this patent involves the reaction of a selected heterocyclic aldehyde, e.g., 3-furaldehyde, 2-thiophenecarboxaldehyde, etc., with cyanotrimethylsilane and zinc iodide to produce, e.g., 2-thiophenesilyl-cyanohydrin, which is reacted with lithium aluminum hydride to produce α-(aminoethyl)-2-thiophenemethanol. This material is then reacted with a ketone, e.g., acetone, methyl ethyl ketone, methyl phenyl ketone, etc., or an aldehyde, e.g., acetaldehyde,furaldehyde, tetrahydrofurfural, etc., to produce the corresponding oxazolidine, e.g., 2,2-dimethyl-5-(2-thienyloxazolidine), which is then reacted with a dihaloacetyl halide, e.g., dichloroacetyl chloride, to obtain the corresponding 5-(dichloroacetyl)-2,2-dimethyl-5-(2-thienyloxazolidine. A process modification disclosed in the U.S. Pat. No. 5,225,570 patent involves the reaction of an α-aminomethyl heterocyclicmethanol, e.g., α-aminomethyl furanemethanol, and an aldehyde, e.g., acetaldehyde, in an inert solvent, e.g., methylene chloride, and an acid acceptor, e.g., pyridine, to form the corresponding oxazolidine, which is then reacted with dichloroacetyl chloride to obtain the final product.

Since the process according to the present invention involves the catalytic hydrogenation of nitroalcohols, brief mention is made of prior work in this area of chemistry. It is well known that nitro groups can be reduced to amines in the presence of hydrogen and a metal catalyst; see, e.g., Rylander, "Catalytic Hydrogenation Over Platinum Metals" Academic Press, New York, 1967. It is further known that amines can be derivatized by treatment with aldehydes and ketones in the presence of hydrogen and a catalyst so that reductive alkylation takes place to give primary, secondary or tertiary amines; see Rylander, ibid, and March, "Advanced Organic Chemistry", Wiley Interscience, New York, 1985.

As a further extension of the above chemistry, it has been shown that reductive alkylation has been carried out on nitro compounds such that they are reduced in situ to primary or secondary amines; see March, ibid, and Emerson, "Organic Reactions, Vol. 4," John Wiley & Sons, New York, 1948. For example, a mixture of nitromethane and acetone with hydrogen and platinum gives methylisopropylamine (see Emerson et al, J. Am. Chem. Soc. 63,749 (1941). Similarly, an alkanolamine, such as ethanolamine, when reacted with acetone, hydrogen and platinum gives N-isopropyl ethanolamine; Cope and Hancock, J. Am. Chemo Soc., 64, 1503 (1942).

Aminoalcohols are difficult to prepare and isolate, because of undesirable by-product formation, such as N-alkylation, as well as promoting reverse reaction ("Retro-Aldol") of the starting nitroalcohol; (U.S. Pat. Nos. 2,347,621, 2,587,572 and 3,564,057).

Therefore, a need exists for a process which could eliminate the need to isolate aminoalcohols in catalytic hydrogenating processes.

Further, the ability to carry out the direct conversion of a nitroalcohol to an oxazolidine compound (useful as an intermediate in the preparation of antidotal 3-dichloroacetyl oxazolidine compounds) would be extremely beneficial due to: (1) the elimination of the need to isolate the intermediate aminoalcohol and oxazolidine starting materials; (2) improvement in reaction cycle times and (3) generally greater process efficiency.

Accordingly, it is an object of this invention to provide a novel process for the catalytic hydrogenation of nitroalcohols in the presence of aldehydes or ketones which avoids undesirable N-alkylation by-products and the need to isolate aminoalcohol, thus permitting in situ reduction and conversion thereof to the corresponding oxazolidine intermediate useful in the production of herbicidal antidote compounds. The achievement of this objective and concomitant advantages is completely new and unexpected.

SUMMARY OF THE INVENTION

The present invention relates to an improved, economical process for producing 3-dihaloacetyl oxazolidine compounds useful as herbicidal antidotes.

More particularly, the process herein involves the simple sequence of reacting selected nitroalcohols with selected aldehydes or ketones to produce the corresponding intermediate oxazolidine, which, in turn, is reacted with a dihaloacetyl halide to obtain as the final product the corresponding 3-dihaloacetyl oxazolidine substituted as desired in the 2–5 positions by use of the appropriate nitroalcohol and carbonyl-containing compound.

In more particular, the invention process involves the catalytic hydrogenation of the nitroalcohol in the presence of the ketone or aldehyde followed by introduction of the dihaloacetyl halide to produce the desired 3-dihaloacetyl-substituted oxazolidine in situ. This in situ process operation provides the advantages of eliminating the need to separate either the intermediate aminoalcohol or oxazolidine compound prior to reacting same with the dihaloacetyl halide (typical of prior art processes).

The invention process is depicted by the following general equation:

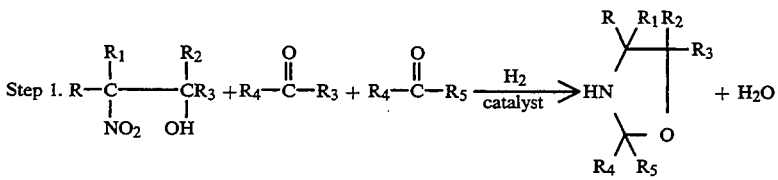
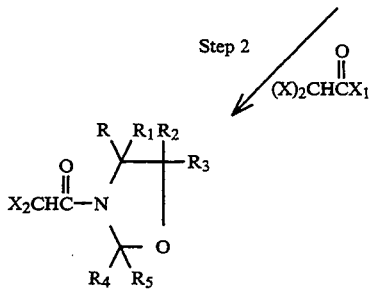

The R and $R_{1-5}$ groups are independently H, $C_{1-6}$ alkyl, haloalkyl, alkylol or alkoxy or alkoxyalkyl having up to 8 carbon atoms, phenyl, benzyl or heterocyclyl having up to 10 carbon atoms and containing O, S and/or N ring atoms and X and $X_1$ are independently halogen, preferably chlorine, bromine or iodine, especially chlorine.

As used herein the term "alkyl" when used alone or in compound form (e.g., "haloalkyl", etc.) includes linear and branched-chain radicals. Preferred alkyl radicals are those having from 1 to 4 carbon atoms.

The heterocyclic member, preferably in the 5-position (i.e., the $R_2$ or $R_3$ member) of Formulae A or B in the above equation, can be saturated or unsaturated and contains from 5 to 10 ring members of which up to 3 can be O, S and/or N atoms. The preferred heterocyclic members are furanyl, thienyl and pyridinyl.

The phenyl, benzyl and heterocyclic members in the above formulae may be substituted (when other than hydrogen) with one or more $C_{1-4}$ alkyl, haloalkyl, alkoxy or alkylol radicals or $C_{2-6}$ alkoxyalkyl, halogen, amino, cyano or nitro groups.

In the above Formulae A and B, the $R_2$ and $R_3$ radicals may be combined and together with the carbon atom to which attached form a $C_{3-6}$ spirocyclic or spiroheterocyclic radical further substituted as with the phenyl, benzyl and heterocyclic members.

Preferred compounds according to Formula A and B are those wherein X is chlorine, R and $R_1$ are hydrogen, $R_2$ or $R_3$ are heterocyclic members as defined above and $R_4$ and $R_5$ are H, $C_{1-4}$ alkyl, haloalkyl alkoxy or $C_{2-4}$ alkoxyalkyl or phenyl groups. The most preferred compounds are those further described and claimed in the above-mentioned U.S. Pat. No. 5,225,570, which is hereby incorporated by reference.

In the catalytic hydrogenation of the nitro-alcohol (Step 1 above), essentially any known hydrogenation catalyst may be used. Preferred catalysts include precious metals such as palladium, platinum, rhodium and ruthenium, and active catalysts, e.g., nickel and other catalysts which are activated by metals such as chromium and molybdenum. These catalysts may be suitably used within the range of 1% to 100% by weight, preferably within the range of 10% to 40% by weight.

The hydrogenation operation herein may be conducted at temperatures within the range of 10°–80° C., preferably within the range of 20°–50° C., and hydrogen pressures ranging from about 0.068–73.0 kg/cm² (atmospheric pressure to 1000 psi) or more, preferably about 3.5 to 28.12 kg/cm² (50–400 psi).

The hydrogenation and dihaloacetylation operations of Steps 1 and 2, respectively, in the above equation may be conducted in any inert solvent, e.g., aliphatic or aromatic hydrocarbon and ether compounds, e.g., hexane, benzene, toluene, etc., acetone, methyl t-butyl ether, etc.

The starting nitroalcohols used in the process of this invention can be prepared by known means, e.g., by reacting the appropriate aldehyde, nitromethane and alcohol. For example, H. B. Hass et al (Industrial and Engineering Chemistry, 43, 2875, (1951), describe a procedure for making 2-nitro-1-phenylethan-1-ol by reacting a solution of benzaldehyde, nitromethane and ethanol with sodium ethoxide and neutralizing the resulting sodium salt with acetic acid to give the desired product in 94.5% yield. Another prior art procedure is found in Hurd C. D.; M. E. Nelson, J. Org. Chem., 1955, 20, 927, wherein acetaldehyde and nitromethane are reacted to give 1-nitro-2-propanol in 70% yield.

DETAILED DESCRIPTION OF THE INVENTION

The following working examples describe various preferred embodiments of the invention:

EXAMPLE 1

A 450 ml stainless steel autoclave was charged with 49 g of a 32.5% wt solution of α-(nitromethyl)-2-furanmethanol in methyl-t-butyl ether (MTBE). To this was added 146 ml of acetone and 3.9 g of active nickel catalyst which had been rinsed once with acetone. The vessel was closed, purged with nitrogen and then pressurized to about 10.6 Kg/cm$^2$ (150 psi) with hydrogen. The reaction mixture was then vigorously stirred while maintaining the temperature at 20°–25° C. A rapid hydrogen uptake was observed. After one hour, the uptake ceased and the mixture was stirred for an additional hour. A sample was withdrawn and analyzed by GC which showed 5-(2-furanyl)-2,2-dimethyloxazolidine to be present in 55% (area). Confirmation was obtained via GC/MS which showed the product peak to have mass/charge (m/e) 167 and a fragmentation pattern identical with authentic material.

EXAMPLE 2

A 450 ml stainless steel autoclave was charged with 49 g of a 32.5% wt solution of α-(nitromethyl)-2-furanmethanol in MTBE. To this was added 146 ml of acetone and 3.9 g of active nickel catalyst which had been rinsed once with acetone. The vessel was closed, purged with nitrogen and then pressurized to about 10.6 kg/cm$^2$ with hydrogen. The reaction mixture was then vigorously stirred while maintaining the temperature at 40° C. A rapid hydrogen uptake was observed. After 80 minutes, the uptake ceased and a sample was withdrawn and analyzed by GC which showed 5-(2-furanyl)-2,2-dimethyloxazolidine to be present in 75% (area).

EXAMPLE 3

A 300 ml stainless steel autoclave, which was configured to allow reactant to be fed in by means of a high pressure feed pump, was charged with 120 ml of acetone and 3.9 g of active nickel catalyst which had been rinsed once with acetone. The vessel was closed, purged with nitrogen and then pressurized to about 10.6 kg/cm$^2$ with hydrogen. The vessel contents were vigorously agitated and 30 ml (27.6 grams) of a 32.5% wt solution of α-(nitromethyl)-2-furanmethanol in MTBE was slowly fed into the vessel at a rate of ~1 ml/minute. The reaction temperature was maintained at 30° C. during addition. Hydrogen uptake was observed during addition. After the addition was completed, the reactor contents were stirred for an additional 90 minutes at 30° C. A sample was then withdrawn and analyzed by GC which showed 5-(2-furanyl)-2,2-dimethyloxazolidine to be present in 88% (area). Confirmation was obtained via GC/MS which showed the product peak to have mass/charge (m/e) 167 and a fragmentation pattern identical with authentic material.

It is well known that activated nickel catalysts in the presence of hydrogen will reduce ketones to alcohols. In Example 3 this reduction was observed to complicate the initial stages of the reduction, consuming some of the acetone and hydrogen and generating unwanted heat. During the course of the reaction this reduction subsided and thereafter only reduction of the nitroalcohol to oxazolidine was observed. In a preferred mode of operation it was found that after addition of about one-fifth of the nitroalcohol charge, reduction of acetone had ceased. Consequently, the improved procedure involves adding an incremental amount, suitably about one-fifth, of the total nitroalcohol charge to the reactor prior to initiating reaction. After reaction of this increment, the balance of the total nitro alcohol charge is then added as illustrated in the following example:

EXAMPLE 4

A 450 ml stainless steel autoclave, which was configured to allow reactant to be fed in by means of a high pressure feed pump, was charged with 134 ml acetone and 12.7 g (dry weight) of a molybdenum-promoted activated nickel catalyst which had been rinsed once with acetone. The vessel was closed, purged with nitrogen and then pressurized to ~7.0 kg/cm$^2$ (100 psi) with hydrogen. With this mixture at ambient temperature 13.7 g of a 46% wt solution of α-(nitromethyl)-2-furanmethanol in MTBE was rapidly pumped into the autoclave. The vessel contents were vigorously agitated while hydrogen uptake and temperature increase to 34° C. were observed. When the exotherm subsided the reactor contents were heated to 40° C. and the remaining 54.6 g of the α-(nitromethyl)-2-furanmethanol solution was slowly fed into the vessel over a period of one hour. The reaction temperature was maintained at 40° C. during addition and hydrogen uptake was observed. At the end of the addition the substrate container and feed lines were washed with 15 ml of additional acetone to complete the transfer of the substrate into the autoclave. The reaction was maintained at 40° C. with stirring for an additional hour. The contents of the reactor were cooled to ambient temperature and filtered away from the catalyst. GC analysis showed 5-(2-furanyl)-2,2-dimethyloxazolidine to be present in 80.2% (area).

EXAMPLE 5

This example exemplifies the conversion of an oxazolidine compound prepared according to the process of this invention into the corresponding dichloroacetyl oxazolidine product which is a known herbicidal antidote compound; this is the Step 2 operation shown in the general equation above.

The reaction mixture from Example 3 was taken and charged to a three neck reaction flask containing 16.8 grams of dry calcium oxide. The slurry was vigorously agitated and 8.8 grams of dichloroacetyl chloride (DCAC) was then slowly added while maintaining the reaction temperature between 25° C.–30° C. by means of an ice bath. The reaction mixture was then stirred for 45 minutes. An additional 1.10 gram of DCAC was added and the mixture stirred for 20 minutes.

The calcium salts were filtered off and the filter cake was rinsed with fresh acetone. The collected filtrates were placed on a rotary evaporator. Solvent was removed under reduced pressure. After ~75% of the solvent volume was removed, 150 ml of water was added to the flask and distillation was continued. After all the volatiles had been removed the resulting solids were collected by vacuum filtration. The collected solids were washed with 20 ml of 1:1 (vol.) isopropyl alcohol/water and dried to give 7.4 g of 3-(dichloroacetyl)-5-(2-furanyl)-2, 2-dimethyloxazolidine. Structure identity was confirmed by proton NMR. Analysis by GC showed the material to be 94.8% (wt) pure.

In a preferred modification of the above Step 2 operation, the reaction mixture of Example 3 is dried by various means, including, but not limited to, the use of drying agents, e.g., alkali metal halides and hydroxides such as NaCl, KOH, etc.; alkaline earth oxides and halides such as barium and calcium chlorides and oxides; other drying means and agents such as molecular sieves, $MgSO_4$, etc., and other drying operations such as azeotropic distillation and other means well known to those skilled in the art.

EXAMPLE 6

Step A. A mixture of 53 g (0.5 mole) benzaldehyde and 33.6 g (0.55 mole) nitromethane was added dropwise to a solution of 20 g (0.5 mole) sodium hydroxide in 200 ml of water so as to maintain a temperature between 0°–5° C. After addition of the mixture was completed, the solution was stirred for 30 minutes. Acetic acid (30.3 g, 0.51 mole) was added to the solution dropwise, maintaining a temperature below ~5° C. The mixture was stirred for another 30 minutes. The solution was then allowed to stand and the organic (bottom) layer was removed. The remaining top layer was extracted with 100 ml MTBE, the bottom layer was removed again and added to the previous one. An aliquot was removed and GC and NMR spectra were obtained. The product obtained was identified as α-nitromethyl benzenemethanol.

Step B. A solution of 2.51 g (0.015 mole) of the product of Step A in 100 ml of acetone was added to 4.11 g Raney nickel in a 450 ml Parr pressure reactor. The mixture was purged with nitrogen and hydrogenated with 7.0 kg/cm² (100 psi) at 40° C. and stirred at 1000 rpm until the pressure curve ceased to fall. During hydrogenation, a further solution of 22.54 g (0.135 mole) of the product of Step A in 25 ml acetone was pump fed into the reactor at a rate of 0.2 ml/min. when there was no further hydrogen uptake the mixture was stirred at 1000 rpm in the reactor for 2 hours at 40° C. The solution was drained out of the reactor, an aliquot was removed and GC and GC-MS were obtained. The product was identified as 2,2-dimethyl-5-phenyl oxazolidine.

EXAMPLE 7

Step A. A mixture of 22.03 g (0.5 mole) acetaldehyde and 33.6 g (0.55 mole) nitromethane was added dropwise to a solution of 20 g (0.51 mole) sodium hydroxide in 200 ml of water so as to maintain a temperature between 0°–5° C. After the addition of the mixture was completed, the solution was stirred for 30 minutes. Acetic acid (30.3 g, 0.5 mole) was added to the solution dropwise, maintaining a temperature below ~5° C. The mixture was then stirred for another 30 minutes. The solution was placed in a separatory funnel and extracted with 100 g MTBE. The mixture was shaken up and allowed to settle. An aliquot of the organic The layer (bottom) was taken and GC spectra were obtained. The product was identified as 1-nitro-2-propanol. The nitroalcohol was not purified or characterised since it could not dissolve in any of the common NMR solvents. The crude product was carried on to the next part of the reaction, Step B.

Step B. A solution of 2.63 g (0.025 mole) 1-nitro-2-propanol in 175 ml acetone was added to 4.31 g Raney nickel in a 450 ml Parr pressure reactor. The mixture was purged with nitrogen and hydrogenated with hydrogen at about 7.0 kg/cm² (100 psi), at 40° C. and stirred at 1000 rpm until the pressure curve ceased to fall. During the hydrogenation, a further solution of 23.62 g (0.225 mol) of 1-nitro-2-propanol in 25 ml acetone was pump fed into the reactor at a rate of 0.2 ml/min. When there was no further hydrogen uptake the mixture was stirred at 1000 rpm in the reactor for an additional 2 hours at 40° C. The solution was drained out of the reactor, and an aliquot was removed and GC-MS were obtained. The product was identified as 2,2,5-trimethyl oxazolidine.

Although this invention has been described with respect to specific embodiments, the details of which are not to be construed as limitations. Various equivalents and obvious modifications will occur to those skilled in the art without departing from the spirit and scope of the invention.

We claim:

1. Process for preparation of compounds according to Formula A

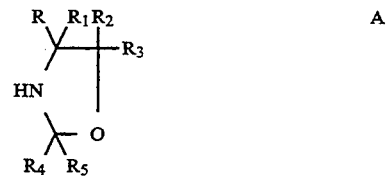

consisting essentially of reacting a nitroalcohol of the formula

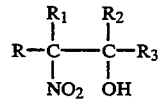

with a ketone having the formula

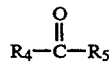

in the presence of hydrogen and a hydrogenation catalyst at temperatures within range of 10°–80° C. and hydrogen pressures within the range of about 0.068 to 73 kg/cm² wherein R, $R_1$ and $R_2$ are independently H, $C_{1-6}$ alkyl, haloalkyl, alkylol or alkoxy or alkoxyalkyl having up to 8 carbon atoms;

$R_3$ is H, or a $C_{1-6}$ alkyl, phenyl, benzyl, furanyl, thienyl, or pyridyl radical and $R_4$ and $R_5$ are independently a $C_{1-6}$ alkyl, haloalkyl, alkylol, alkoxy or alkoxyalkyl radical having up to 8 carbon atoms; provided the alkyl portion of said radicals is linear alkyl.

2. Process according to claim 1 wherein said nitroalcohol is introduced into a reaction zone in an initial incremental amount and allowed to react prior to adding the remaining charge of nitroalcohol.

3. Process according to claim 2 wherein R, $R_1$ and $R_2$ are hydrogen, $R_3$ is said furanyl, thienyl or pyridyl radical and $R_4$ and $R_5$ are independently H, $C_{1-4}$ alkyl or haloalkyl.

4. Process according to claim 3 wherein the compound of Formula A is 2,2-dimethyl-5-(2-furanyl)oxazolidine.

5. Process according to claim 3 wherein the compound of Formula A is 2,2-dimethyl-5-(2-thienyl)oxazolidine.

6. Process according to claim 3 wherein the compound of Formula A is 2,2-dimethyl-5-(3-pyridyl)oxazolidine.

7. Process according to claim 1 wherein said compound of Formula A is further reacted with a dihaloacetyl halide compound to form the corresponding 3-dihaloacetyl-(un)substituted oxazolidine according to Formula B.

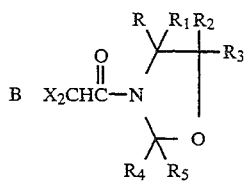

wherein
R and $R_1$–$R_5$ are as defined in claim 1 and X is halogen.

8. Process according to claim 7 wherein the halogen group in Formula B is chlorine.

9. Process according to claim 8 wherein the compound of Formula B is the 3-dichloroacetyl oxazolidine of a compound according to any of claims 5–7.

10. Process according to claim 9 wherein said compound of Formula B is 3-dichloroacetyl-2,2-dimethyl-5-(2-furanyl)oxazolidine.

* * * * *